(12) United States Patent
Markert et al.

(10) Patent No.: US 7,129,205 B2
(45) Date of Patent: Oct. 31, 2006

(54) DIMETHYLBENZENE DERIVATIVES

(75) Inventors: Thomas Markert, Monheim (DE); Werner Faber, Willich (DE); Theo Ten Pierik, Venlo (NL)

(73) Assignee: KAO Corporation, Tokyo (JP)

( * ) Notice: Subject to any disclaimer, the term of this patent is extended or adjusted under 35 U.S.C. 154(b) by 279 days.

(21) Appl. No.: 10/332,220

(22) PCT Filed: Jun. 23, 2001

(86) PCT No.: PCT/EP01/07156
§ 371 (c)(1),
(2), (4) Date: Jan. 3, 2003

(87) PCT Pub. No.: WO02/02494
PCT Pub. Date: Jan. 10, 2002

(65) Prior Publication Data
US 2003/0148918 A1    Aug. 7, 2003

(30) Foreign Application Priority Data
Jul. 4, 2000  (DE) ................. 100 32 335

(51) Int. Cl.
*A61Q 13/00* (2006.01)
(52) U.S. Cl. .......................... 512/20; 512/25
(58) Field of Classification Search ............. 512/20, 512/25
See application file for complete search history.

(56) References Cited

U.S. PATENT DOCUMENTS 3,590,103 A    6/1971  Tieman et al.
6,376,457 B1   4/2002  Markert et al.

FOREIGN PATENT DOCUMENTS

| DE | 1 920 672 A | 11/1969 |
|----|---|---|
| DE | 197 14 041 A | 10/1998 |
| FR | 1 538 619 A | 9/1968 |
| JP | 2001348308 | * 12/2001 |
| WO | WO 98/45236 | 10/1998 |

OTHER PUBLICATIONS

E. Glyde, R. Taylor: "Electrophilic Aromatic Reactivities via Pyrolysis of 1-Arylethyl Acetates", Journal of the Chemical Society, Perkin Transactions 2., 1977, pp. 1537-1541, XP002186110, Chemical Society. Letchworth., GB, ISSN: 1472-779X, Darstellung von, 1-(2,4-Dimethylphenyl) ethylacetat, p. 1540.

* cited by examiner

*Primary Examiner*—Monique T. Cole
(74) *Attorney, Agent, or Firm*—Oblon, Spivak, McClelland, Maier & Neustadt, P.C.

(57) ABSTRACT

Compounds of the formula (I):

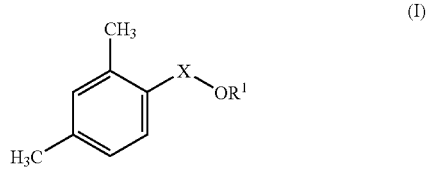

wherein X is a —(C=CH$_2$)— group or a —CH(CH$_3$)— group, with the proviso that when X is a —(C=CH$_2$)— group, R$^1$ is a C$_{1-10}$ alkyl group or a C$_{2-10}$ alkenyl group and when X is a —CH(CH$_3$)— group, R$^1$ is hydrogen, a saturated or unsaturated, linear or a branched C$_{1-10}$ alkyl group, a C$_{1-10}$ acyl group, a C$_{1-10}$ cycloalkyl group or an aryl group are useful as perfumes.

2 Claims, No Drawings

DIMETHYLBENZENE DERIVATIVES

This invention relates to new dimethylbenzene derivatives and to their use as perfumes.

PRIOR ART

Judging by demand, many natural perfumes are available in totally inadequate quantities. For example, 5,000 kg of rose blossoms are required to produce 1 kg of rose oil. The consequences are extremely limited annual world production and a high price. Accordingly, it is clear that there is a constant need in the perfume industry for new perfumes with interesting fragrance notes. On the one hand, the range of naturally available perfumes can be extended in this way; on the other hand, it is thus possible to make the necessary adaptations to changing fashion trends. In addition, it is possible in this way to meet the steadily increasing demand for odor enhancers for products of everyday use, such as cosmetics and cleaners.

In addition, there is generally a constant need for synthetic perfumes which can be favorably produced in a consistent quality and which have desirable olfactory properties, i.e. in particular pleasant, near-natural and qualitatively new odor profiles of adequate intensity, and which are capable of advantageously influencing the fragrance of cosmetic and consumer products. In other words, there is a constant need for compounds which have characteristic new odor profiles coupled with high staying power, intensity of odor and emanative power.

DESCRIPTION OF THE INVENTION

It has been found that the compounds corresponding to general formula (I) excellently satisfy the above-mentioned requirements in every respect and may advantageously be used as perfumes with differently nuanced perfume notes characterized by high staying power.

In a first embodiment, the present invention relates to dimethylbenzene derivatives corresponding to general formula (I):

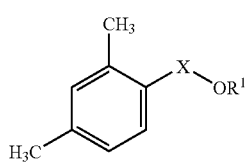

(I)

in which X is a —(C=CH$_2$)— group or a —CH(CH$_3$)— group, with the proviso that
  if X is a —(C=CH$_2$)— group, the substituent R$^1$ is a C$_{1-10}$ alkyl group or a C$_{2-10}$ alkenyl group and
  if X is a —CH(CH$_3$)— group, the substituent R$^1$ is hydrogen, a C$_{1-10}$ alkyl group which may be saturated or unsaturated, linear or branched, a C$_{1-10}$ acyl group, a C$_{1-10}$ cycloalkyl group or an aryl group.

In another embodiment, the invention relates to the use of dimethylbenzene derivatives corresponding to general formula (I) above as perfumes. The following compounds are preferred:
  1(1-ethoxyvinyl)-2,4-dimethylbenzene,
  1-(2,4-dimethylphenyl)-ethanol,
  1-(1-ethoxyethyl)-2,4-dimethylbenzene,
  1-(2,4-dimethylphenyl)-ethylacetate.

The compounds (I) according to the invention are distinguished by an odor characteristic in which anthranilate notes and flowery and musk notes dominate. They show excellent stability in cosmetic and consumer perfumery formulations.

The compounds (I) may be prepared by known synthesis processes of organic chemistry.

In perfume compositions, the compounds (I) strengthen harmony, emanation, naturalness and also staying power, the quantities used being adapted to the particular perfume note required taking the other ingredients of the composition into account.

The fact that the compounds (I) have the above-mentioned perfume notes was not foreseeable and, hence, is further confirmation of the general experience that the olfactory properties of known perfumes do not allow any definitive conclusions to be drawn as to the properties of structurally related compounds because neither the mechanism of odor perception nor the influence of chemical structure on odor perception has been sufficiently researched, so that it is not normally possible to predict whether modifications to the structure of known perfumes will in fact lead to changes in their olfactory properties or whether these changes will be positive or negative.

By virtue of their odor profile, the compounds corresponding to formula (I) are also particularly suitable for modifying and enhancing known compositions. Particular emphasis is placed on their extreme intensity of odor which contributes quite generally towards refining the composition.

The compounds corresponding to formula (I) may be combined with many known perfume ingredients, for example other perfumes of natural, synthetic or partly synthetic origin, essential oils and plant extracts. The range of natural fragrances can thus include both high-volatility and also medium-volatility and low-volatility components while the range of synthetic perfumes may include representatives of virtually every class of compounds.

Examples of suitable substances with which the compounds (I) may be combined are, in particular,
(a) natural products, such as tree moss absolue, basil oil, citrus oils, such as bergamot oil, mandarin oil, etc., mastix absolue, myrtle oil, palmarosa oil, patchouli oil, petitgrain oil, wormwood oil, myrrh oil, olibanum oil
(b) alcohols, such as farnesol, geraniol, linalool, nerol, phenylethyl alcohol, rhodinol, cinnamic alcohol, sandalore [3-methyl-5-(2,2,3-trimethylcyclopent-3-en-1-yl)-pentan-2-ol], sandela [3-isocamphyl-(5)-cyclohexanol]
(c) aldehydes, such as citral, Helional®, α-hexyl cinnamaldehyde, hydroxycitronellal, Lilial® [p-tert.butyl-α-methyidihydrocinnamaldehyde], methylnonyl acetaldehyde
(d) ketones, such as allylionone, α-ionone, β-ionone, isoraldein, methyl ionone
(e) esters, such as allylphenoxyacetate, benzyl salicylate, cinnamyl propionate, citronellyl acetate, decyl acetate, dimethylbenzyl carbinyl acetate, ethyl acetoacetate, hexenyl isobutyrate, linalyl acetate, methyl dihydrojasmonate, vetiveryl acetate, cyclohexyl salicylate
(f) lactones, such as gamma-undecalactone, 1-oxaspiro[4.4]-nonan-2-one and various other components often used in perfumery, such as musk and sandalwood perfumes, indole, p-methan-8-thiol-3-one, methyl eugenol and Ambroxan.

It is also remarkable how the compounds corresponding to formula (I) round off and harmonize the odor notes of a broad range of known compositions without unpleasantly dominating them in any way. 1(1-ethoxyvinyl)-2,4-dimethylbenzene, 1-(2,4-dimethylphenyl)-ethanol, 1-(1-ethoxyethyl)-2,4-dimethylbenzene and 1-(2,4-dimethylphenyl)-ethylacetate are particularly emphasized in this regard.

The compounds (I) according to the invention or mixtures thereof may be used in perfume compositions in quantities of about 1 to 70% by weight, based on the mixture as a whole. Mixtures of compounds (I) according to the invention and compositions of this type may be used both for perfuming cosmetic preparations, such as lotions, creams, shampoos, soaps, ointments, powders, aerosols, toothpastes, mouthwashes, deodorants, and also in alcohol-based perfumery (for example colognes, toilet waters, extracts). The compounds according to the invention or mixtures thereof may also be used for perfuming commercial products, such as detergents, fabric softeners and textile treatment preparations. For perfuming these various products, the compositions are added in an olfactorily effective quantity, more particularly in a concentration of 0.05 to 2% by weight, based on the product as a whole. However, these values are not intended to represent limits because the experienced perfumer can also obtain effects with even lower concentrations or can build up new complexes with even higher doses.

EXAMPLES

Example 1

Preparation of 1-(2,4-dimethylphenyl)-ethanol

Materials:
a) 296 g (2 mol) 2,4-dimethylacetophenone (Cognis)
b) 318 g (2.2 mol) Vitride (70% in toluene)
c) 300 ml toluene, water-free Apparatus:
2-liter four-necked flask with stirrer, thermometer and reflux condenser, inert gas.

Method: 296 g 2,4-dimethyl acetophenone and 300 ml toluene dried over molecular sieve were mixed under nitrogen in the reaction flask. 318 g Vitride solution were then added dropwise over 3.5 hours with vigorous stirring and cooling with an ice bath. The temperature of the mixture rose to 48° C. Gas chromatographic conversion control showed 3% educt and 92.1% product. The reaction mixture was then stirred for another 2 hours at room temperature.

Working up: After cooling to room temperature, 600 ml 10% sodium hydroxide were carefully added over ca. 3 hours to the mixture stirred under nitrogen. A vigorous evolution of hydrogen was initially observed. The mixture was transferred to a 5-liter separation funnel and the water phase was removed. The toluene phase was washed once with 10% sodium hydroxide and twice with saturated sodium chloride solution, dried over sodium sulfate and concentrated in a rotary evaporator.

125 g crude product were distilled in a 20 cm Vigreux column. 108 g distillate with a GC purity of 93% were obtained at a boiling point of 83–84° C./0.15 mbar.

Analysis: The $^1$H-NMR spectrum (280 MHz, in $CDCl_3$) showed 1 doublet (1 methyl group) at chemical shifts of 1.4 ppm and 2 singlets (1 methyl group for each) at 2.3 ppm. 1 Multiplet (1 H) appeared at 5.1 ppm and the 3 aromatic protons at 6.9, 7.0 and 7.4 ppm.

The IR spectrum (film between NaCl) showed C—O bands at 1007, 1078 and 1128 $cm^{-1}$ and a broad signal for the —OH vibration at 3345 $cm^{-1}$ with a shoulder at 3550 $cm^{-1}$.

Odor characteristic: Initial perfume: animaly, indole, salicylate notes; after-perfume (after 24 hours on a test strip): indole, animaly, anthranilate, salicylate notes.

Example 2

Preparation of 1-(1-ethoxyethyl)-2,4-dimethylbenzene

Materials:
a) 111.0 g (0.5 mol) 2,4-dimethylacetophenone diethylketal (prepared in accordance with WO 98/45236)
b) 100 ml ethanol, water-free
c) 2.5 g 5% palladium/carbon Apparatus: 1-liter steel autoclave insert, lift-stirrer high-pressure autoclave Method: Components a), b) and c) were successively weighed under nitrogen into a 1-liter steel autoclave insert. In the autoclave, the mixture was first purged with nitrogen, after which the autoclave was brought to 60 bar with hydrogen. The autoclave was heated to 100° C. and then brought to 100 bar with hydrogen first half-hourly and later hourly. After 4.5 hours, no further uptake of hydrogen was observed, the reaction mixture was heated for 0.5 hour, cooled and vented. The catalyst was filtered off and the reaction mixture was concentrated in a rotary evaporator. 60.4 g crude product were distilled in a 20 cm Vigreux column. 19.6 g 1-ethyl-2,4-dimethylbenzene (Bp. 33° C./0.07 mbar, purity: 96.7%) as secondary product and 22.5 g main product [1-(1-ethoxyethyl)-2,4-dimethylbenzene] with a GC purity of 92.2% were obtained at a boiling point of 45–50° C./0.07 mbar.

Analysis: The $^1$H-NMR spectrum (280 MHz, in $CDCl_3$) showed 2 singlets (2 methyl groups) at chemical shifts of 2.2 ppm, 1 doublet (1 methyl group) at 1.4 and one triplet (1 methyl group) at 1.1 ppm. A doublet of the quadruplet (1 methylene group) appeared at 3.3 ppm and a quadruplet (1H) at 4.6 ppm. The 3 aromatic protons produced resonances with the typical coupling pattern of the 1,2,4-substitution at 6.9; 7.0 and 7.3 ppm.

The IR spectrum (film between NaCl) showed broad ether bands at 1065, 1093, 1118 and 1154 $cm^{-1}$.

Odor characteristic: Initial perfume: flowery, fruity, Eau de Cologne, musk notes; after-perfume: anthranilate, salicylate, indole notes.

Example 3

Preparation of 1-(2,4-dimethylphenyl)-ethylacetate

Materials:
a) 90.0 g (0.6 mol) 1-(2,4-dimethylphenyl)-ethanol (prepared in accordance with Example 1)
b) 200 g acetanhydride
c) 0.5 g 4-N,N-dimethylaminopyridine (Aldrich)

Apparatus: 1-liter four-necked flask with stirrer, internal thermometer, reflux condenser and dropping funnel.

Method: a) and c) were weighed into the reactor and b) was continuously added dropwise in 40 minutes at room temperature. An increase in the temperature of the mixture to 40° C. was observed. By cooling with a water bath, the temperature of the reaction mixture was kept at 40° C. until b) had been completely added. After b) had been completely added, the reaction mixture was stirred for 3 hours and then left standing overnight at room temperature.

Working up: Excess acetanhydride and acetic acid were distilled off in a water jet vacuum. The residue was diluted with 100 ml of cyclohexane and washed with saturated sodium bicarbonate solution and with water until neutral, dried over sodium sulfate and concentrated in a rotary evaporator.

95 g crude product were distilled in a 20 cm Vigreux column. 56 g distillate were obtained; the main quantity had a GC purity of 97.9% for a boiling point of 77–80° C./0.15 mbar.

Analysis: The $^1$H-NMR spectrum (280 MHz in CDCl$_3$) showed 1 doublet (1 methyl group) at a chemical shift of 1.5 ppm and 3 singlets (3 methyl groups) at 2.0, 2.3 and 2.35 ppm. A quadruplet (1H) appeared at 6.0 ppm and the 3 aromatic protons at 6.9, 7.0 and 7.25 ppm.

The IR spectrum (film between NaCl) showed sharp vibration bands at 1236 (C—O) and 1738 (C=O) cm$^{-1}$.

Odor characteristic: Initial perfume: jasmone, anthranilate, musk, anise notes, after-perfume (after 24 hours on a test strip): faint woody, jasmone note.

Example 4

Preparation of 1(1-ethoxyvinyl)-2,4-dimethylbenzene

Materials:
a) 100.1 g 2,4-dimethylacetophenone (Cognis)
b) 110.9 g triethyl orthoformate
d) 0.21 g sulfuric acid, conc.
e) 191.4 g ethanol, 96%

Apparatus: 1-liter four-necked flask with stirrer, thermometer and jacketed coil condenser, inert gas.

Method: Components a), b) and d) were introduced into the flask under nitrogen and in the absence of moisture. Component c) was carefully added with vigorous stirring. The mixture was stirred for 3 hours at room temperature and then neutralized with 0.54 g triethanolamine (pH 7). In addition, the pH was adjusted to 8 with another 0.44 g triethanolamine.

Working up: The reaction mixture was freed from ethanol, formic acid ester and triethyl orthoformate in a rotary evaporator.

149.1 g crude product were distilled in a 20 cm Vigreux column, the main quantity (48.2 g, 97.8%) distilling over at 72–73°C./0.03 mbar.

Yield: 82.4% of the theoretical.

Analysis: The $^1$H-NMR (400 MHz, in d6-DMSO) showed 1 triplet at 1.3 ppm (1 methyl group) and 2 singlets at 2.2 ppm (2 methyl groups). In addition, a quadruplet (1 methylene group) appeared at 3.8 ppm. The two olefinic protons appeared as singlets at 4.1 and 4.3 ppm and the 3 aromatic protons with the characteristic splitting pattern at 6.9, 7.0 and 7.1 ppm.

Odor characteristic: Initial perfume flowery, orange blossom, honey, anthranilate, indole, nitromusk notes; after-perfume (after 24 hours on a test strip): salicylate, anthranilate note.

What is claimed is:

1. A perfume composition comprising a compound of the formula (I):

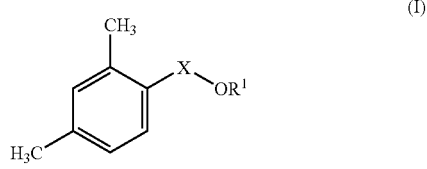

wherein X is a —(C=CH$_2$)— group or a —CH(CH$_3$)— group, with the proviso that when X is a —(C=CH$_2$)— group, R$^1$ is a C$_{1-10}$ alkyl group or a C$_{2-10}$ alkenyl group and when X is a —CH(CH$_3$)— group, R$^1$ is hydrogen, a saturated or unsaturated, linear or a branched C$_{1-10}$ alkyl group, a C$_{1-10}$ acyl group, a C$_{1-10}$ cycloalkyl group or an aryl group.

2. The composition of claim 1 wherein the concentration of the compound of formula (I) is from 1 to 70% by weight.

* * * * *